(12) United States Patent
Reid (10) Patent No.: US 11,805,997 B2
(45) Date of Patent: Nov. 7, 2023

(54) SKIN BIOPSY DEVICE

(71) Applicant: Revedeon, LLC, Waterloo, IA (US)

(72) Inventor: Alexander Thomas Reid, Iowa City, IA (US)

(73) Assignee: Revedeon, LLC, Waterloo, IA (US)

( * ) Notice: Subject to any disclaimer, the term of this patent is extended or adjusted under 35 U.S.C. 154(b) by 347 days.

(21) Appl. No.: 17/089,461

(22) Filed: Nov. 4, 2020

(65) Prior Publication Data

US 2021/0137505 A1 May 13, 2021

Related U.S. Application Data

(60) Provisional application No. 62/933,513, filed on Nov. 10, 2019.

(51) Int. Cl.
*A61B 10/02* (2006.01)

(52) U.S. Cl.
CPC .. *A61B 10/0275* (2013.01); *A61B 2010/0208* (2013.01)

(58) Field of Classification Search
CPC .............. A61B 10/0275; A61B 2010/0208
See application file for complete search history.

(56) References Cited

U.S. PATENT DOCUMENTS

| 4,699,154 A | 10/1987 | Lindgren |
| 4,924,878 A | 5/1990 | Nottke |
| 4,944,308 A | 7/1990 | Akerfeldt |
| 5,036,860 A | 8/1991 | Leigh et al. |
| 5,172,702 A | 12/1992 | Leigh et al. |
| 5,183,053 A | 2/1993 | Yeh et al. |
| 5,284,156 A | 2/1994 | Schramm et al. |
| 5,842,999 A | 12/1998 | Pruitt et al. |
| 9,861,345 B2 | 1/2018 | Cao et al. |
| 10,219,790 B2 | 3/2019 | Grillo Fernandez et al. |
| 2005/0101912 A1* | 5/2005 | Faust ................ A61M 5/158 604/117 |
| 2005/0149092 A1* | 7/2005 | Dunn ............... A61B 10/0266 606/185 |
| 2005/0165403 A1* | 7/2005 | Miller .............. A61B 10/025 600/567 |
| 2005/0267502 A1 | 12/2005 | Hochman |
| 2009/0018467 A1 | 1/2009 | Chiu et al. |
| 2013/0096458 A1 | 4/2013 | Schraga |
| 2015/0073300 A1 | 3/2015 | Cao et al. |

(Continued)

FOREIGN PATENT DOCUMENTS

EP 1968455 A2 9/2008

*Primary Examiner* — Rene T Towa (57) ABSTRACT

Devices and methods for performing a skin biopsy are discussed herein. The skin biopsy device provides for consistent depth and shape, such as by reducing or eliminating operator error or inter-operator variability by generating the same forces across multiple uses. The skin biopsy device can also eliminate puckering of wound closures by incorporating a fusiform blade (e.g., elliptical blade or a diamond-shaped blade). The skin biopsy device includes a casing, a firing pin, a retaining rod, and a blade. The retaining rod holds the blade or can attach to a punch biopsy. The firing pin generates and impacts the retaining rod with a force necessary to drive the blade a given depth into a target tissue to obtain a biological sample.

20 Claims, 7 Drawing Sheets

(56) References Cited

U.S. PATENT DOCUMENTS

| | | | |
|---|---|---|---|
| 2016/0058431 A1* | 3/2016 | Holzer | A61B 17/00491 |
| | | | 600/570 |
| 2016/0354065 A1* | 12/2016 | Grillo Fernandez | ........................ |
| | | | A61B 17/32053 |
| 2018/0249988 A1* | 9/2018 | Neal | A61B 10/0266 |

* cited by examiner

SKIN BIOPSY DEVICE

CROSS-REFERENCE TO RELATED APPLICATIONS

This application claims the benefit of U.S. Provisional Patent Application Ser. No. 62/933,513, filed Nov. 10, 2019, the contents of which are herein incorporated by reference in their entirety.

BACKGROUND

A method of performing a skin biopsy and the device for performing the skin biopsy have remained generally unchanged for many years. Currently, a skin biopsy is performed by hand using a device that creates a circular hole in the skin of the patient. However, there are issues associated with the current method and device.

The first issue is the operating variability from operator to operator. The variability can result in differing results, including improper biopsies (e.g., not enough tissue, a damaged sample, or the like), improper healing, or the like. Operating variables can include, without limitation, downward and rotational forces exerted on the device during insertion into the skin. For example, operators can vary in the amount of downward force and rotational force when performing a biopsy.

The second issue is puckering. When closing the wound that results from the skin biopsy, a circular hole can pucker (i.e., draw or gather into wrinkles or irregular folds) due to wound edges that do not properly align. The puckering can result in scarring, improper healing, or the like.

The state of the art can benefit with an improved skin biopsy device.

DETAILED DESCRIPTION

Devices and methods for performing a skin biopsy are discussed herein. The skin biopsy device provides for consistent depth and shape, such as by reducing or eliminating operator error or inter-operator variability by generating the same forces across multiple uses. The skin biopsy device can also eliminate puckering of wound closures by incorporating a fusiform blade (e.g., elliptical blade or a diamond-shaped blade). Eliminating operator error, inter-operator variability, wound closure puckering, the like, or combinations or multiples thereof can increase the number of usable samples, improve healing, reduce scarring, the like, or combinations or multiples thereof.

The operator uses a loaded device to generate the necessary force to make the biopsy. The device also allows for improved visualization of the blade when performing the biopsy, thereby seeing exactly where the blade is making contact with a target tissue prior to engaging the device and as the blade enters the target tissue.

The device can also be reusable and sterilized or disinfected using readily available chemicals or methods. The only component that is changed out is the blade.

The blade can also be reset to be used on the same patient multiple times or be reused in the same location to make a deeper incision over top of the first incision. For example, after using the device, the operator simply re-cocks a firing pin via a handle while keeping the original blade loaded on the device. The device can then be used again in a different location. Or, the device can be used in the same location to alter the existing excision in terms of depth, shape, size, the like, or combinations or multiples thereof.

The device can also allow operators to adjust a depth of cut. A limiter can be adjusted to a desired height, thereby restricting the depth by which the blade enters the target tissue.

The skin biopsy device includes a casing, a firing pin, a retaining rod, and a blade. The casing houses components of the skin biopsy device, adjoins with other components of the skin biopsy device, and provides structural integrity for the skin biopsy device. The retaining rod holds the blade or can attach to a punch biopsy. The firing pin generates and impacts the retaining rod with a force necessary to drive the blade a given depth into a patient's skin to obtain a biological sample.

The blade can be fusiform (i.e., a shape that is wider in the middle and tapered or tapers towards the ends or edges). The fusiform blade reduces or eliminates puckering by providing a wound having edges that, when closed, can properly align. In one example, the blade is elliptical. In another example, the blade is diamond-shaped.

In another example, the blade is a punch biopsy having a grip and a cutting surface extending from the grip.

Though the devices and methods are discussed with regards to the skin (i.e., epidermis, dermis, hypodermis, or combinations thereof), the devices and methods can be used for biopsies from the subcutis, muscles, or other biological tissue or organ.

Figure 1A:
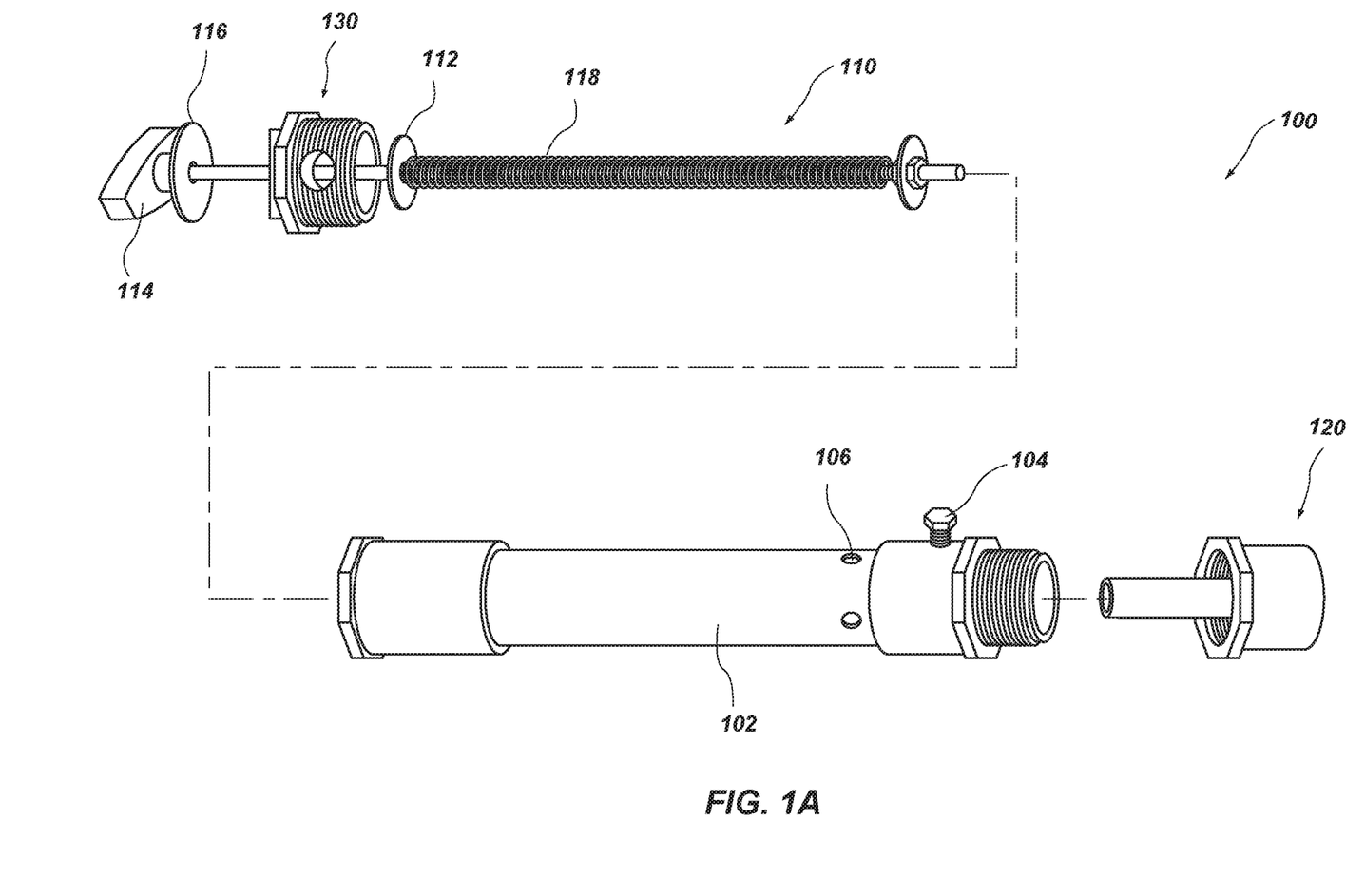
FIG. 1A illustrates an example skin biopsy device having been partially disassembled.
Figure 1B:
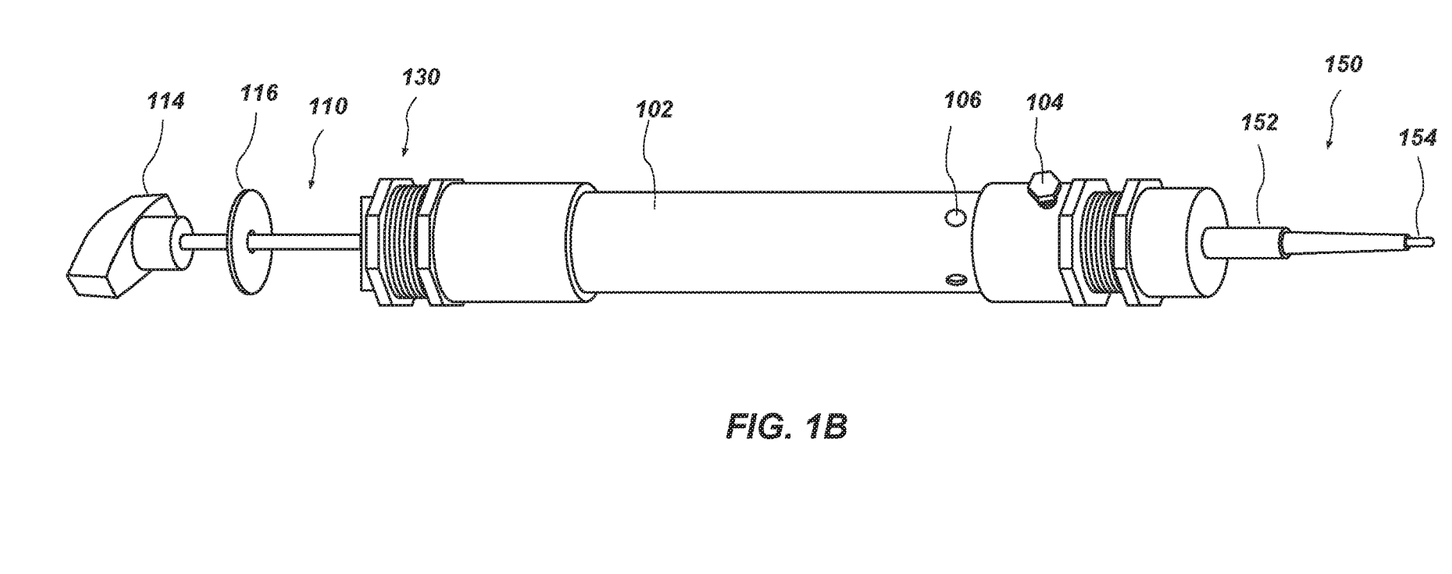
FIG. 1B illustrates the example skin biopsy device having been assembled.

FIG. 1A shows a skin biopsy device 100 in a partially disassembled construction. FIG. 1B shows the skin biopsy device 100 in an assembled construction with a punch 150. The skin biopsy device 100 includes a casing 102, a firing pin 110, a retaining rod (not shown), a limiter 120, and a blade 154. A collar 130 and a handle 114 are located at or proximal to a first end of the casing 102. The limiter 120 is located at or proximal to a second end of the casing 102.

The casing 102 houses components of the skin biopsy device 100, adjoins with other components of the skin biopsy device 100, provides structural integrity for the skin biopsy device 100, and provides a surface for an operator to grip or hold during operation of the skin biopsy device 100. In one example, the retainer (not shown) can be attached to the punch 150. The punch 150 includes a shaft 152 attached to the blade 154. In another example, the retainer (not shown) can be attached to a blade.

Figure 2:
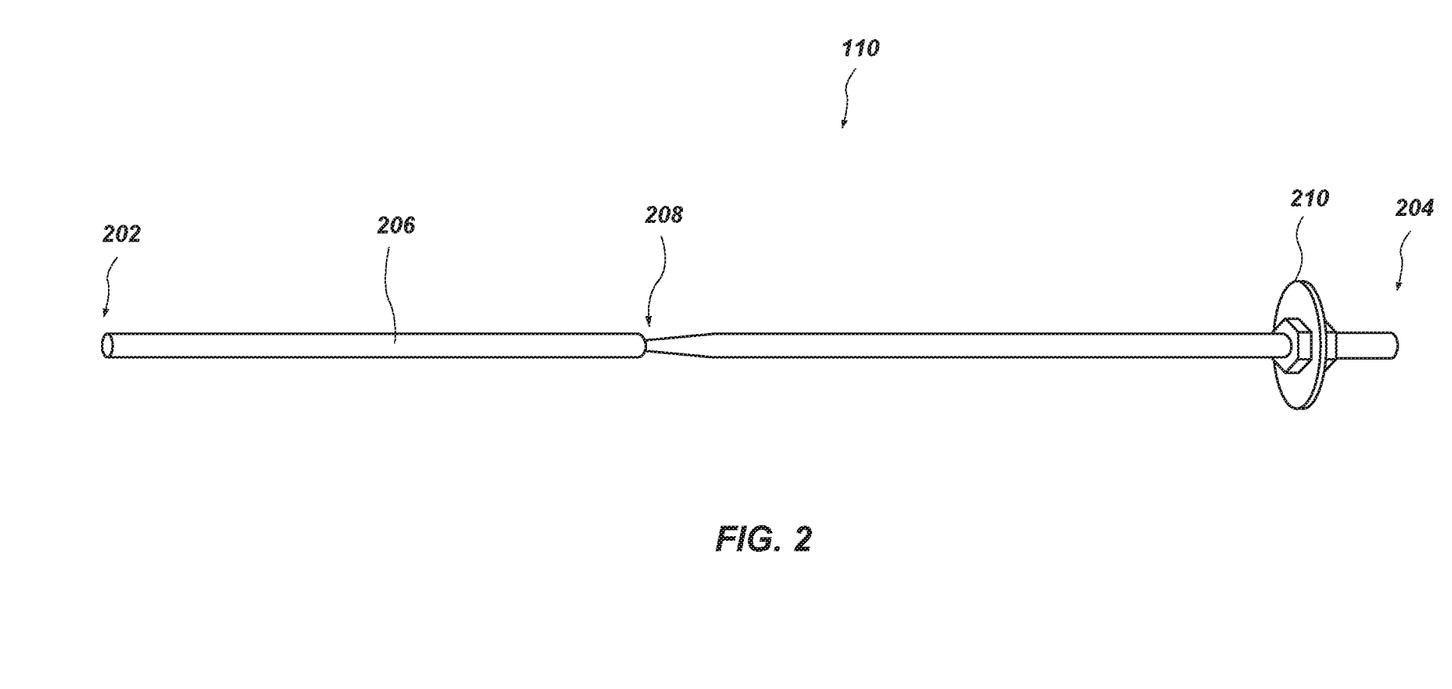
FIG. 2 illustrates an example firing pin of the example skin biopsy device.

The firing pin 110 generates and impacts the retainer (not shown), such as at an enlarged end of the retainer (not shown), with a force necessary to drive the blade 154 a given depth into the target tissue (e.g., patient's skin) to obtain a sample. The firing pin 110 can extend the entire length of the casing 102 or a portion thereof. FIG. 2 shows the firing pin 110. The firing pin 110 includes a first end 202 and an impact end 204 adjoined by a main body 206. To reduce damage to the retainer (not shown), the impact end 204 can include a dampener or can be composed of a material for dampening. For example, the impact end 204 can include or be formed from a polymer (e.g., rubber).

The firing pin 110 can include a notch 208 at a point along the length of the main body 206. The notch 208 can provide a surface or catch against which the collar 130 or a release (not shown) can secure the firing pin 110 and prevent the firing pin 110, when in a cocked position, from travelling to a released or uncocked position. The notch 208 can extend circumferentially around the main body 206, can extend partially around the main body 206, can be a detent, can be multiple detents on opposing sides of the main body 206, or the like. In one example, the main body 206 can include threads on the entirety of its length. In another example, the main body 206 can includes threads on a portion of its length. In yet another example, the main body 206 does not include threads.

The firing pin 110 also includes a protrusion 210 proximal to the impact end 204. The protrusion 210 extends around the entire circumference of the main body 206 or around a partial circumference of the main body 206. In one example, the length of the main body 206 from the impact end 204 to the protrusion 210 is based on a distance to be traveled by the blade 154 into the target tissue.

Returning to FIG. 1, the protrusion 210 provides a surface against which a spring 118 can rest or press. The spring 118, which surrounds a portion of the firing pin 110, can be compressed when the firing pin 110 is in the cocked position. To bring the firing pin 110 into the cocked position, a handle 114 is drawn away from the limiter 120.

The spring 118, when in tension (i.e., the compressed state), stores potential energy (i.e., based on a spring constant and a distance of compression). Therefore, when the firing pin 110 is released, the spring 118 expands and presses on the protrusion 210, thereby converting the potential energy to kinetic energy. The kinetic energy causes the firing pin 110 to accelerate towards the retainer (not shown). The firing pin 110 strikes the enlarged end of the retention rod with a force based on the acceleration of the firing pin 110 caused by conversion of the potential energy of the spring 118 into the kinetic energy.

In one example, the protrusion 210 also provides a surface to contact a restraint 104 (e.g., a screw, rod, post, rivet, or the like). The protrusion 210 therefore does not travel further than the restraint 104, which further limits travel of the firing pin 110 and the blade 154. The restraint 104 can also provide a backstop for the retainer (not shown) to prevent movement of the retainer (not shown) towards the handle 114.

In one example, the restraint 104 can pass through a sidewall of the casing 102 via a hole 106. The casing 102 can include multiple holes into which the restraint 104 can be inserted. In another example, the restraint 104 can be internal to the casing 102 with the height adjustable by a slidable tab external to the casing 102.

The firing pin 110 can also include a spring limiter 112 to limit the travel of the spring 118 when placed in tension (i.e., compressed).

Figure 3:
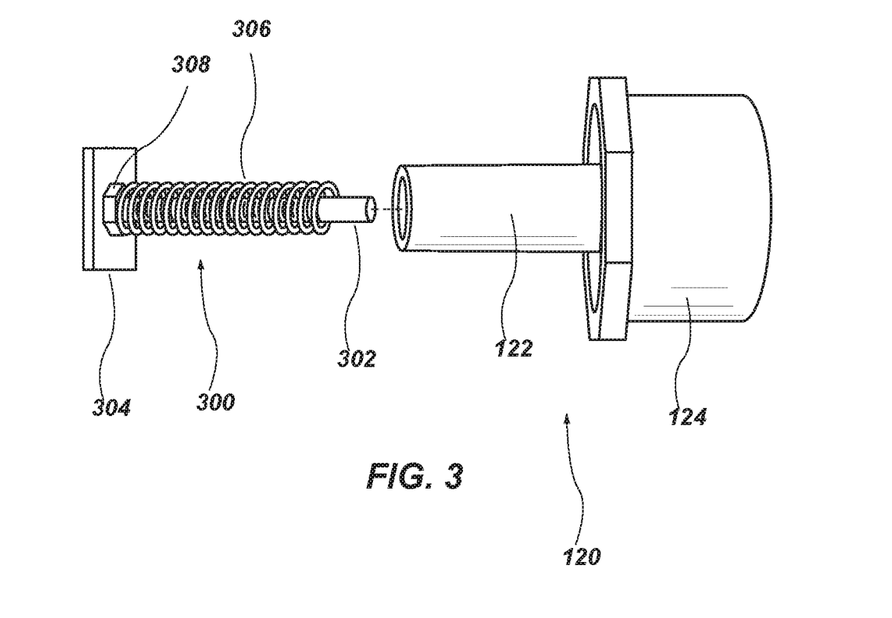
FIG. 3 illustrates an example limiter of the example skin biopsy device.

The skin biopsy device 100 also includes the limiter 120. FIG. 3 shows the limiter 120. The limiter 120 includes a base 124 and contact column 122. The base 124 can attach the limiter 120 to the casing 102, such as by an attachment mechanism (e.g., threads or detents) or by a press fit. The distance by which the limiter 120 extends away from the casing 102 can be adjusted to provide a pre-determined depth for the blade 154 to travel into the target tissue. The adjustment of the limiter 120 can be continuous (i.e., a retainer 300 can travel any distance from 0.1 millimeters to 3 centimeters) or can be discrete (i.e., the retainer 300 can travel any distance from 0.1 millimeters to 3 centimeters, with the limiter 120 being moveable in increments of 0.1 mm, 0.2 mm, 0.5 mm, or the like).

The retainer 300 engages with the contact column 122 via a spring 306 or the enlarged end 304. A retention rod 302 can extend at least partially into and through the contact column 122 and the base 124. The spring 306 can be located around the retention rod 302 or a portion thereof. In one example, the spring 306 can inhibit translation or movement of the retention rod 302, the punch 150, or both prior to being struck by the firing pin 110 upon release from the cocked position.

In one example, such as to reduce travel of the retention rod 302, the spring 306 engages with an upper surface of the contact column 122. In another example, such as to reduce travel of the retention rod 302, the enlarged end 304 engages with an upper surface of the contact column 122, whether the spring 306 is present or not.

The retainer 300 includes an enlarged end 304 distal to an end which passes into the contact column 122. The enlarged end 304 absorbs the impact from the firing pin 110, which causes the retainer 300 to travel towards the limiter 120.

The enlarged end 304 can be sized and shaped to fit within an internal cavity of the casing 102. In one example, the enlarged end 304 can be shaped to inhibit rotation of the retainer 300 relative to the casing 102. Inhibiting rotation of the retention rod, such as when the blade is fusiform, prevents damaging the sample or causing a larger wound to the target tissue than necessary. In another example, when the enlarged end 304 matches the shape of the internal cavity of the casing 102 (e.g., both are circular, rectangular, squares, or the like), the retainer 300 can include a stabilizer 308 to prevent rotation of the retention rod relative to the casing 102 and the limiter 120. The stabilizer 308 can be shaped to inhibit rotation (i.e., a square or rectangle when an internal cavity of the limiter 120 is circular), can be a tongue or groove with the complementary groove or tongue in a sidewall of the limiter 120, or the like.

Figure 4:
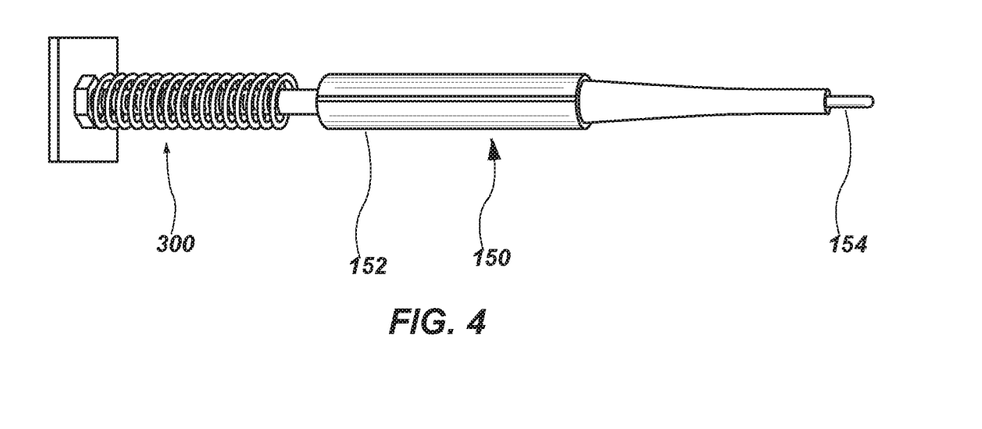
FIG. 4 illustrates an example retainer with an example blade.

FIG. 4 shows the retainer 300 attached to the punch 150. The blade 154 can be circular.

In one example, the end of the retaining rod 302 which adjoins to the punch 150 can be straight. In another example, the end of the retaining rod 302 which adjoins to the punch 150 can be tapered. The taper permits punches with different internal shaft diameters to be used. The retention rod 302 can be inserted via a press fit. In yet another example, the end of the retaining rod 302 which adjoins to the punch 150 can be threaded.

Figure 5A:
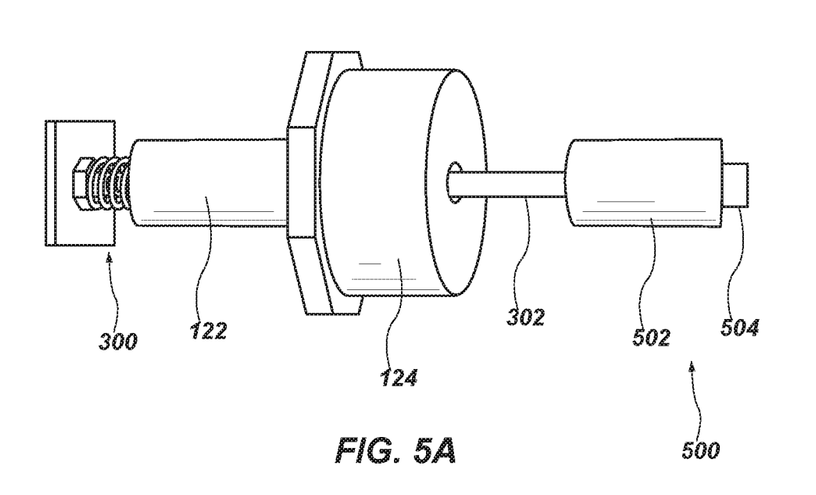
FIG. 5A illustrates an example retainer with an example blade.
Figure 5B:
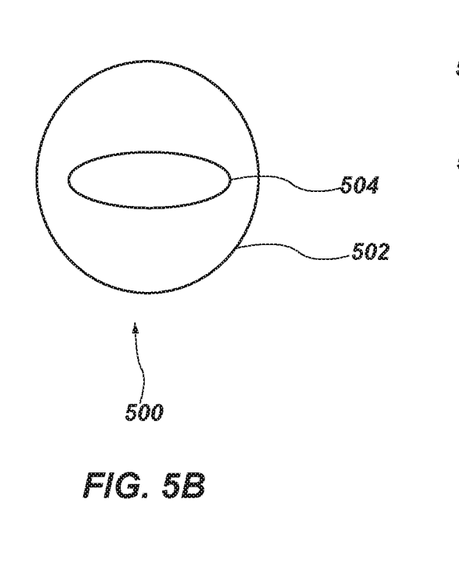
FIG. 5B illustrates an example blade.
Figure 5C:
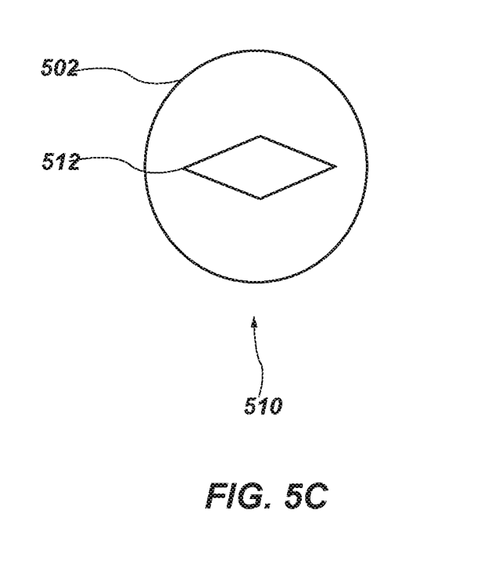
FIG. 5C illustrates an example blade.

FIG. 5A shows the retainer 300 attached to a cutter 500. The cutter 500 includes a connector 502 and a blade 504. The end of the retaining rod 302 which adjoins to the cutter 500 can be straight, tapered, threaded, the like, or combinations or multiples thereof. The blade 504 can be fusiform. In one example, the blade 504 is elliptical (FIG. 5B). In another example, a cutter 510 includes a blade 512 that is diamond-shaped (FIG. 5C).

Figure 6:
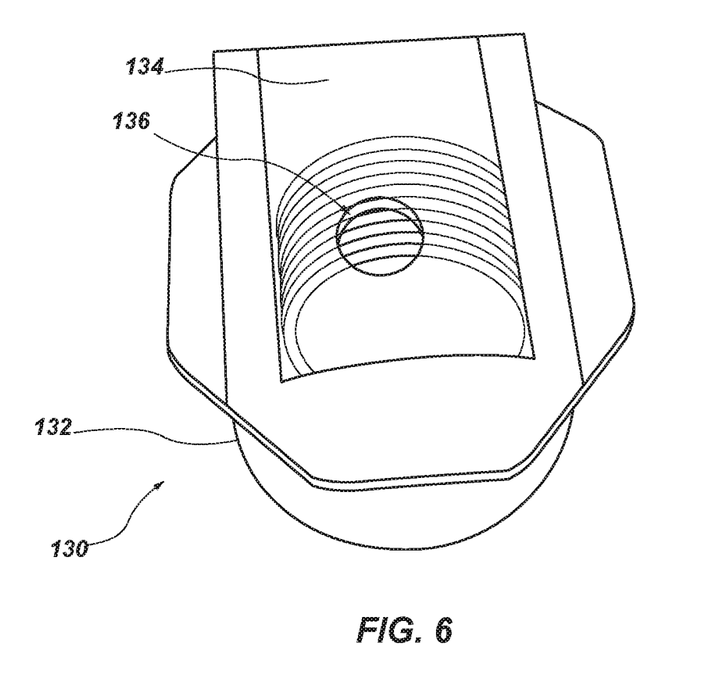
FIG. 6 illustrates an example collar.

FIG. 6 shows the collar 130. The collar 130 includes a catch and a base 132. The base 132 can adjoin the collar 130 to the casing 102 via press fit, threads, or the like. The catch is a plate 134 having a hole 136 extending through the plate 134. The notch 208 of the firing pin 110 is pulled through the hole 136. The notch 208 rests on a surface of the plate 134. An operator then presses on the firing pin 110 via an actuator 116, such as with a handle, knob, projection, or the like, to cause the notch 208 to pass back through the hole 136. The spring 118, having been initially compressed, expands and causes the firing pin 110 to accelerate towards the retainer 300.

To operate the skin biopsy device 100, the punch 150 can be loaded onto the retention rod 302. The handle 114 is pulled back until the notch 208 locks into or onto the catch of the collar 130. The blade 154 of the punch 150 can then be placed over the area of the target tissue to be biopsied. The actuator 116 is then pushed to align the firing pin 110 and cause the notch 208 to move back through the hole 136. The spring 118, having been in compression when the handle 114 is pulled back, exerts a force on the protrusion 210 which causes the firing pin 110 to move towards the limiter 120. The impact end 204 strikes the enlarged end 304 of the retainer 300. The retainer 300, which includes the punch 150 attached or adjoined thereto, moves toward the target tissue. In one example, the spring 306 contacts the upper surface of the contact column 122. The blade 154 of the punch 150 then enters the target tissue at a depth that is set by the limiter 120. The spring 306, being compressed between the upper surface of the contact column 122 and the enlarged end 304, inhibits the retention rod 302 and the punch 150 from traveling further than the depth provided by the limiter 120. The skin biopsy device 100 is then lifted away after the incision has been made. The punch 150 can be removed from the retaining rod 302. In another example, the enlarged end 304 contacts the upper surface of the contact column 122. The blade 154 of the punch 150 then enters the target tissue at a depth that is set by the limiter 120. The enlarged end 304, being compressed against the upper surface of the contact column 122, inhibits the retention rod 302 and the punch 150 from traveling further than the depth provided by the limiter 120. The skin biopsy device 100 is then lifted away after the incision has been made. The punch 150 can be removed from the retaining rod 302.

Figure 7:
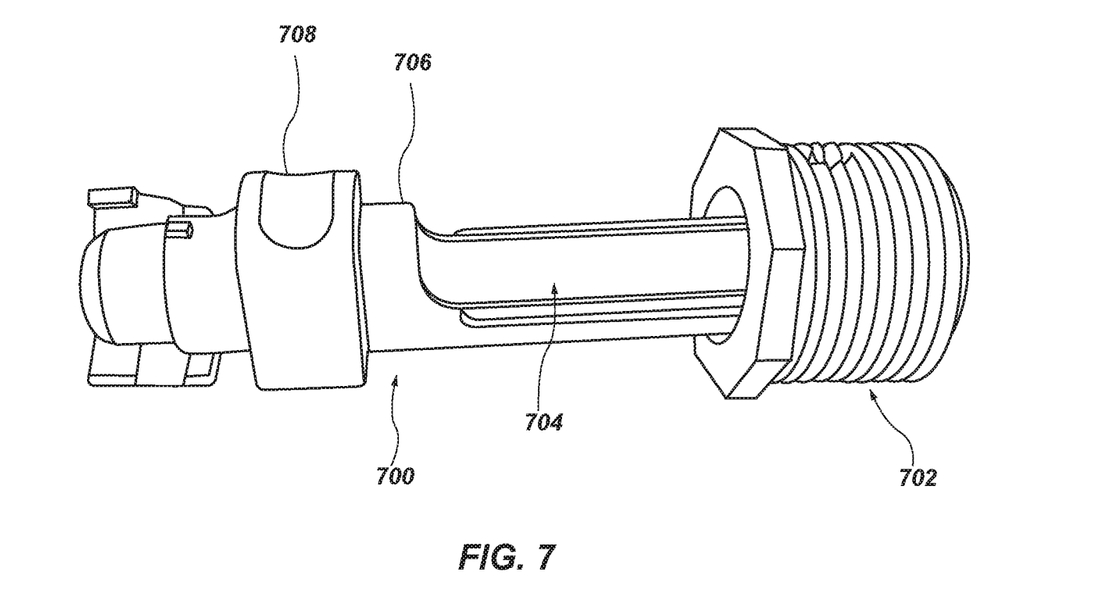
FIG. 7 illustrates an example release.

FIG. 7 shows a release 700. The release 700 includes a main body 706 having a cavity 704 extending therethrough to receive the firing pin 110 or a portion thereof. The release 700 also includes a connector 702 to adjoin the release 700 to the casing 102. The release 700 also includes a button 708 to engage the notch 208 for locking and releasing purposes. When the firing pin 110 is cocked, an operator can press the button 708 which releases the notch 208. The spring 118, having been initially compressed, expands and causes the firing pin 110 to accelerate towards the retainer 300.

The cavity 704 can also include a spring (not shown) to engage and exert a force on the button 708 when the notch 208 is locked by the button 708.

Figure 8:
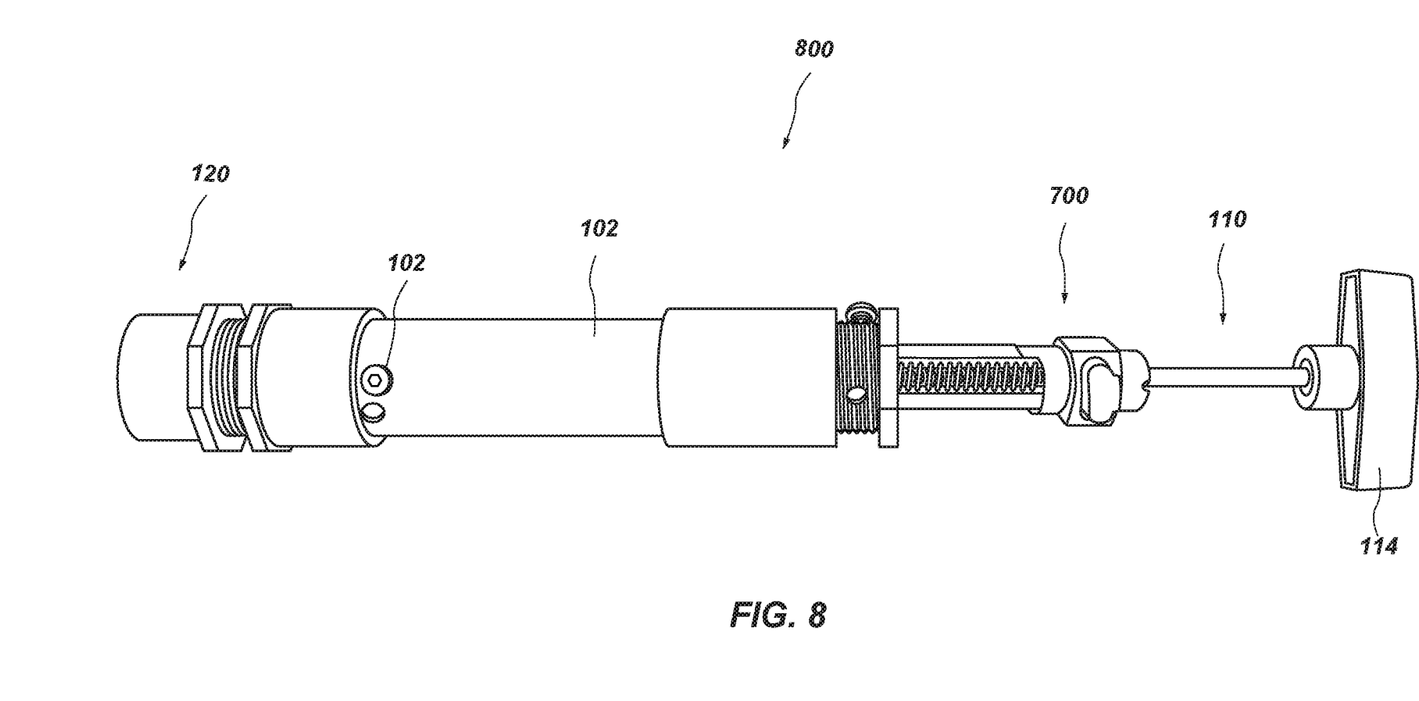
FIG. 8 illustrates an example skin biopsy device with the example release.

FIG. 8 shows a skin biopsy device 800. The skin biopsy device 800 is similar to the skin biopsy device 100, except that the release 700 has replaced the collar 130.

Operation of the skin biopsy device 800 is similar to the operation of skin biopsy device 100, except for using the button 708 to release the notch 208 of the firing pin 110 when in tension or the cocked position. For purposes of this operation, the punch 150, as previously discussed, is replaced by the cutter 500. To operate the skin biopsy device 100, the cutter 500 can be loaded on the retention rod 302. The handle 114 is pulled back until the notch 208 engages with the button 708. The button 708, for example, can be flush with the main body 706 when not engaged with the notch 208. The button 708 can then pop out and extend outwardly from the main body 706 when the button 708 catches and engages the notch 208. The blade 504 can then be placed over the area of the target tissue to be biopsied. The button 708 is then pushed to release the notch 208. The spring 118, having been in compression when the handle 114 is pulled back, exerts a force on the protrusion 210 which causes the firing pin 110 to move towards the limiter 120. The impact end 204 strikes the enlarged end 304 of the retainer 300. The retainer 300, which includes the cutter 500 attached or adjoined thereto, moves toward the target tissue. The spring 306 contacts the upper surface of the contact column 122. The blade 504 then enters the target tissue at a depth that is set by the limiter 120. The spring 306, being compressed between the upper surface of the contact column 122 and the enlarged end 304, inhibits the retention rod 302 and the cutter 500 from traveling further than the depth provided by the limiter 120. The skin biopsy device 100 is then lifted away after the incision has been made. The cutter 500 can be removed from the retaining rod 302.

The skin biopsy device 100, 800 can be composed of metal, plastic, polymer, epoxy, adhesive, wood, foam, metal alloys, the like, or combinations or multiples thereof.

Though one or more springs are discussed herein, other components, mechanisms, or devices to retain a component, exert or absorb forces, or the like on one or more other components can be used, included, or incorporated therein. These other force mechanisms can include, without limitation, a clasp, a dampener, a piston, the like, or combinations or multiples thereof.

Though certain elements, aspects, components or the like are described in relation to one embodiment or example, such as an example skin biopsy device, those elements, aspects, components or the like can be including with any other skin biopsy device, such as when it desirous or advantageous to do so.

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific embodiments are presented by way of examples for purposes of illustration and description. They are not intended to be exhaustive of or to limit this disclosure to the precise forms described. Many modifications and variations are possible in view of the above teachings. The embodiments are shown and described in order to best explain the principles of this disclosure and practical applications, to thereby enable others skilled in the art to best utilize this disclosure and various embodiments with various modifications as are suited to the particular use contemplated. It is intended that the scope of this disclosure be defined by the following claims and their equivalents:

What is claimed is:

1. A skin biopsy device, comprising:
    a firing pin including
        a main body having a first end and an impact end,
        a protrusion extending at least partially around a circumference of the main body, and
        a spring surrounding a portion of the main body and in contact with the protrusion;
    a retainer including
        a first stabilizer,
        a retention rod having a first end and an enlarged end, the enlarged end to absorb a force when struck by the impact end of the firing pin, and a spring surrounding at least a portion of the retention rod;

a blade attached to the first end of the retention rod; and a limiter including a contact column having a second stabilizer on an inner surface, the contact column to provide a surface for the spring of the retainer to contact to limit a distance by which the blade travels, wherein the first and second stabilizers are complementary and engage with each other to inhibit rotation of the retainer.

2. The skin biopsy device of claim 1, further comprising a handle connected to the first end of the firing pin.

3. The skin biopsy device of claim 2, wherein the spring of the firing pin is placed in a compressed state when the handle is pulled away from the limiter into a cocked position.

4. The skin biopsy device of claim 3, wherein the main body of the firing pin further comprises a notch.

5. The skin biopsy device of claim 4, further comprising a collar including a plate with a hole extending through the plate to form a catch that engages the notch of the firing pin when the firing pin is in the cocked position.

6. The skin biopsy device of claim 5, wherein the firing pin further comprises an actuator.

7. The skin biopsy device of claim 6, wherein when the notch moves back through the hole, the spring, having been released from the compressed state to an uncompressed state, drives the firing pin towards the enlarged end of the retainer.

8. The skin biopsy device of claim 4, further comprising a release including a button to engage the notch of the firing pin when the firing pin is in the cocked position.

9. The skin biopsy device of claim 8, wherein when the button disengages the notch, the spring, having been released from the compressed state to an uncompressed state, drives the firing pin towards the enlarged end of the retainer.

10. The skin biopsy device of claim 2, further comprising a casing having a first end and a second end, the limiter being proximal to the second end and the handle being proximal to the first end.

11. The skin biopsy device of claim 10, wherein the casing further comprises a restraint in contact with the protrusion of the firing pin.

12. The skin biopsy device a claim 11, wherein the restraint extends through a sidewall of the casing via a hole.

13. The skin biopsy device of claim 12, wherein the restraint is a screw, a rod, a post, or a rivet.

14. The skin biopsy device of claim 12, wherein the casing further comprises a plurality of holes, each of the plurality of holes being placed at different points along a length of the casing to adjust the distance of the restraint relative to the second end.

15. The skin biopsy device of claim 11, wherein the restraint is internal to the casing, a position of the restraint being adjustable along a length of the casing by a slidable tab external to the casing.

16. The skin biopsy device of claim 1, wherein the blade is fusiform.

17. The skin biopsy device of claim 16, wherein the blade is elliptical.

18. The skin biopsy device of claim 17, wherein the blade is diamond-shaped.

19. The skin biopsy device of claim 1, wherein the first and second stabilizers are a tongue and groove system.

20. The skin biopsy of claim 1, wherein the first and second stabilizers are shaped to prevent rotation of the first stabilizer relative to the second stabilizer.

* * * * *